United States Patent
Ishikawa et al.

(10) Patent No.: US 8,524,940 B2
(45) Date of Patent: Sep. 3, 2013

(54) NITRO GROUP-CONTAINING ETHER COMPOUND AND METHOD FOR PRODUCING SAME

(75) Inventors: Teruhiko Ishikawa, Okayama (JP); Seiki Saito, Okayama (JP); Takayuki Kudoh, Okayama (JP); Kotaro Suto, Okayama (JP); Hironori Nishiuchi, Okayama (JP); Makoto Okada, Okayama (JP); Masatoshi Taniguchi, Okayama (JP)

(73) Assignee: National University Corporation Okayama University, Okayama (JP)

( * ) Notice: Subject to any disclaimer, the term of this patent is extended or adjusted under 35 U.S.C. 154(b) by 29 days.

(21) Appl. No.: 13/312,150

(22) Filed: Dec. 6, 2011

(65) Prior Publication Data
US 2012/0130092 A1 May 24, 2012

Related U.S. Application Data

(63) Continuation-in-part of application No. PCT/JP2010/059889, filed on Jun. 4, 2010, and a continuation-in-part of application No. PCT/JP2010/060002, filed on Jun. 8, 2010.

(30) Foreign Application Priority Data

| Jun. 9, 2009 | (JP) | 2009-138720 |
| Jul. 9, 2009 | (JP) | 2009-162840 |
| Jul. 9, 2009 | (JP) | 2009-162969 |
| Sep. 4, 2009 | (JP) | 2009-204883 |

(51) Int. Cl.
*C07C 205/05* (2006.01)
*C07C 69/003* (2006.01)
*C07C 61/22* (2006.01)

(52) U.S. Cl.
USPC .......................... 560/125; 560/128; 562/507

(58) Field of Classification Search
USPC ............................. 562/507; 560/125, 128
See application file for complete search history.

(56) References Cited

U.S. PATENT DOCUMENTS

| 5,720,895 A | 2/1998 | Nakagawa et al. |
| 2006/0047002 A1 | 3/2006 | Karpf et al. |

FOREIGN PATENT DOCUMENTS

| CN | 101020646 | 8/2007 |
| JP | 8-104687 | 4/1996 |
| JP | 9-241206 | 9/1997 |
| JP | 2008-511568 | 4/2008 |

OTHER PUBLICATIONS

International Search Reports issued Jul. 27, 2010 in International (PCT) Application No. PCT/JP2010/060002 and PCT/JP2010/059889.
D. B. Killian et al., "The Synthesis of Some Dioxole Derivatives from Alkylacetylenes", Journal of the American Chemical Society, vol. 58, pp. 1658-1659, 1936.
P. R. Krishna et al., "The Baylis-Hilman Reaction: A Strategic Tool for the Synthesis of Higher-Carbon Sugars", Tetrahedron Letters, vol. 48, No. 37, pp. 6466-6470, 2007.
R. I. Hollingsworth et al., "Taming Carbohydrate Complexity: A Facile, High-Yield Route to Chiral 2,3-Dihydroxybutanoic Acids and 4-Hydroxytetrahydrofuran-2-ones with Very High Optical Purity from Pentose Sugars", Journal of Organic Chemistry, vol. 64, No. 20, pp. 7633-7634, 1999.
Supplementary European Search Report dated Oct. 25, 2012 in Application No. 10786262.5.
S. Nakamura et al., "Total Synthesis of Zaragozic Acid C by an Aldol-Based Strategy", Tetrahedron, vol. 61, pp. 11078-11106, 2005.
M. Karpf et al., "New, Azide-Free Transformation of Epoxides into 1,2-Diamino Compounds: Synthesis of the Anti-Influenza Neuraminidase Inhibitor Oseltamivir Phosphate (Tamiflu)", J. Org. Chem., vol. 66, No. 6, pp. 2044-2051, 2001.
L. Wang et al., "Formation of Carbocycles by Intramolecular Conjugate Displacement: Scope and Mechanistic Insights", Journal of American Chemical Society, vol. 131, No. 16, pp. 6003-6012, 2009.

*Primary Examiner* — Noble Jarrell
*Assistant Examiner* — Valerie Rodriguez-Garcia
(74) *Attorney, Agent, or Firm* — Wenderoth, Lind & Ponack, L.L.P.

(57) ABSTRACT

It is possible to produce oseltamivir safely and stably in large quantities by using as a starting material tartaric acid, mannitol or arabinose, via dihydroxyhexenoic acid ester of the formula (4c):

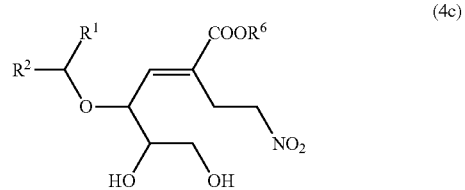

(wherein $R^1$, $R^2$ and $R^6$ are same or different and are each alkyl, aryl, substituted aryl, aralkyl, substituted aralkyl or aromatic heterocyclic group, and $R^1$ and $R^2$ are not methyl simultaneously).

4 Claims, No Drawings

NITRO GROUP-CONTAINING ETHER COMPOUND AND METHOD FOR PRODUCING SAME

This application is a continuation-in-part of International Application Ser. Nos. PCT/JP2010/059889 filed Jun. 4, 2010 and PCT/JP2010/060002 filed Jun. 8, 2010.

TECHNICAL FIELD

The present invention relates to a nitro group-containing ether compound and processes for producing the same.

BACKGROUND ART

Oseltamivir inhibits the liberation of an influenza virus from the infected cell surface by inhibiting neuraminidase (NA) which is an enzyme, and it is known to restrain infection and increase to other cells and is a useful compound.

As a method of preparing oseltamivir, it is known those using as a starting material quinic acid or shikimic acid which is a cyclic hydroxyacid found in a cinchona (Patent Literature 1). However, these acids are naturally occurring compounds and their supply is limited, and are unsuitable to obtain oseltamivir in large quantities. In addition, there are problems in production to use an azide reagent or an azide intermediate which is toxic and explosive.

In producing oseltamivir, in view of using the azide reagent which is toxic and explosive, it is disclosed a method which does not use the azide reagent (Patent Literature 2).

However, in producing oseltamivir, it is desired to provide a process for producing oseltamivir safely and stably in large quantities with use of an extremely abundant compound as a starting material and without use of an azide reagent or an azide intermediate which is toxic and explosive.

Prior Art Documents
Patent Literature
Patent Literature 1: JP2000-517306A
Patent Literature 2: JP2001-031631A

SUMMARY OF THE INVENTION

Problem to be Solved by the Invention

An object of the present invention is to provide a nitro group-containing ether compound which is an intermediate useful for producing oseltamivir safely and stably in large quantities, and a process for producing the compound.

Means for Solving the Problem

The present invention provides the following.

1. A nitro group-containing ether compound of the formula (1).

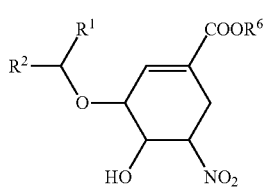

(wherein $R^1$, $R^2$ and $R^6$ are same or different and are each alkyl, aryl, substituted aryl, aralkyl, substituted aralkyl or aromatic heterocyclic group, and $R^1$ and $R^2$ are not methyl simultaneously)

2. A compound as defined in above 1 wherein $R^1$, $R^2$ and $R^6$ are same or different and are each straight-chain, branched chain or cyclic alkyl having 1 to 8 carbon atoms, aralkyl having 7 to 20 carbon atoms or aralkyl having 7 to 20 carbon atoms and having a substituent, and $R^1$ and $R^2$ are not methyl simultaneously, the substituent of aralkyl having 7 to 20 carbon atoms being selected from among alkyl having 1 to 8 carbon atoms, alkoxyl having 1 to 8 carbon atoms, halogen atom, hydroxyl, amino and trifluoromethyl.

3. A compound of the formula (2).

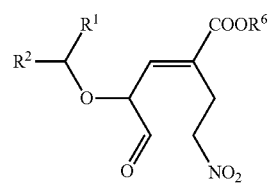

(wherein $R^1$, $R^2$ and $R^6$ are the same as above 1)

4. A compound as defined in above 3 wherein $R^1$, $R^2$ and $R^6$ are same or different and are each straight-chain, branched chain or cyclic alkyl having 1 to 8 carbon atoms, aralkyl having 7 to 20 carbon atoms or aralkyl having 7 to 20 carbon atoms and having a substituent, and $R^1$ and $R^2$ are not methyl simultaneously, the substituent of aralkyl having 7 to 20 carbon atoms being selected from among alkyl having 1 to 8 carbon atoms, alkoxyl having 1 to 8 carbon atoms, halogen atom, hydroxyl, amino and trifluoromethyl.

5. A process for preparing compound (2) comprising subjecting a dihydroxyhexenoic acid ester of the formula (4c) to diol-cleavage reaction.

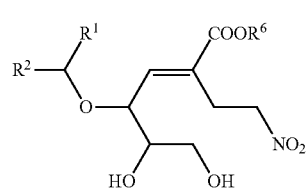

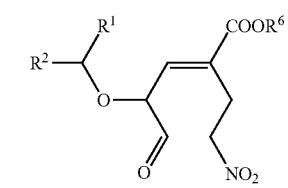

(wherein $R^1$, $R^2$ and $R^6$ are same as above 1)

6. A process for preparing compound (1) comprising subjecting a compound of the formula (2) to intramolecular nitroaldol reaction.

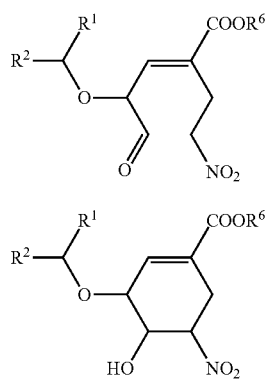

(wherein $R^1$, $R^2$ and $R^6$ are same as above 1)

7. A process for preparing compound (3) comprising reducing compound (1).

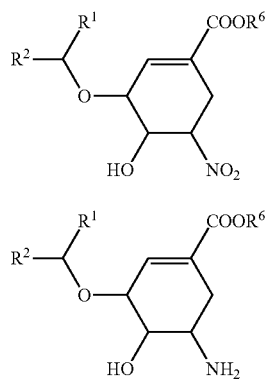

(wherein $R^1$, $R^2$ and $R^6$ are same as above 1)

8. A compound of the formula (4c).

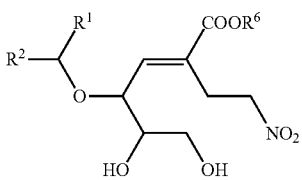

(wherein $R^1$, $R^2$ and $R^6$ are same as above 1)

9. A compound of the formula (2ab).

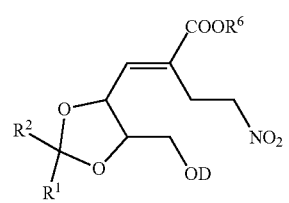

(wherein $R^1$, $R^2$ and $R^6$ are same as above 1, D is hydrogen atom or protective group of hydroxyl)

10. A compound of the formula (3ab).

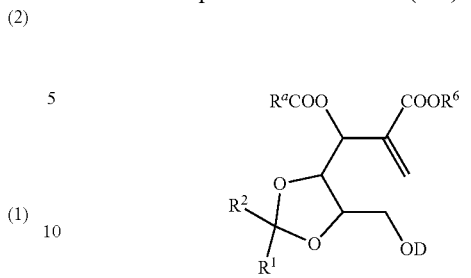

(wherein $R^1$, $R^2$ and $R^6$ are same as in above 1, D is same as in above 9, $R^a$ is alkyl, aryl, substituted aryl, aralkyl, substituted aralkyl or aromatic heterocyclic group)

11. A compound of the formula (4ab).

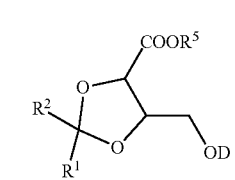

(wherein $R^1$, $R^2$ are same as in above 1, D is same as in above 9, $R^5$ is alkyl, aryl, substituted aryl, aralkyl, substituted aralkyl or aromatic heterocyclic group)

12. A compound of the formula (5).

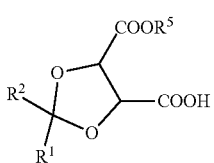

(wherein $R^1$ and $R^2$ are same as in above 1, $R^5$ is same as in above 11)

13. A compound of the formula (6).

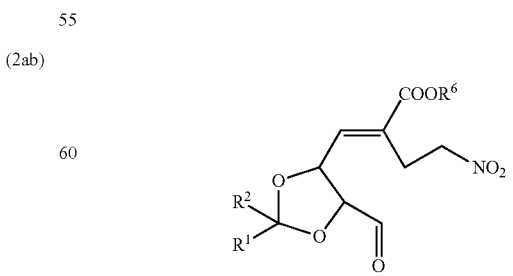

(wherein $R^1$, $R^2$ and $R^6$ are same as in above 1)

14. A compound of the formula (7).

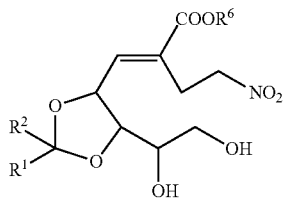
(7)

(wherein $R^1$, $R^2$ and $R^6$ are same as in above 1)

15. A compound of the formula (8).

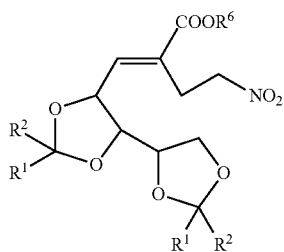
(8)

(wherein $R^2$, $R^2$ and $R^6$ are same as in above 1)

16. A compound of the formula (9).

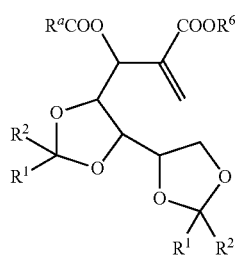
(9)

(wherein $R^1$, $R^2$ and $R^6$ are same as in above 1, $R^a$ is same as in above 10)

17. A compound of the formula (10).

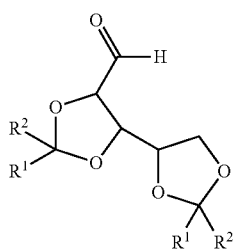
(10)

(wherein $R^1$ and $R^2$ are same as in above 1)

18. A compound of the formula (12).

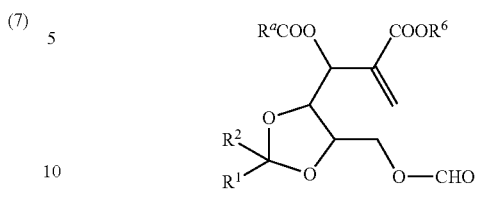
(12)

(wherein $R^1$, $R^2$ and $R^6$ are same as in above 1, $R^a$ is same as in above 10)

19. A compound of the formula (13).

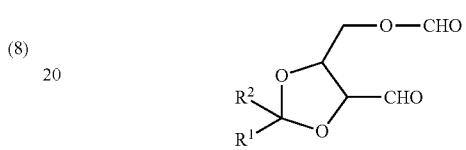
(13)

(wherein $R^1$ and $R^2$ are same as in above 1)

20. A compound of the formula (14).

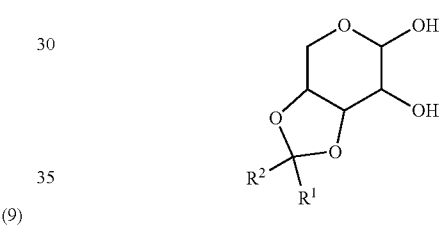
(14)

(wherein $R^1$ and $R^2$ are same as in above 1)

Effects of the Invention

Nitro group-containing ether compound of the present invention can be prepared by using as a starting material D-tartaric acid, mannitol or arabinose which is present in extremely abundant quantities as natural source or industrial material. It is possible to produce oseltamivir safely and stably in large quantities with use of this ester.

Embodiments of Practicing the Invention

The present invention relates to a novel nitro group-containing ether compound which is an important precursor of oseltamivir, and a process for producing the compound.

Nitro group-containing ether compound of the present invention is represented by the formula (1)

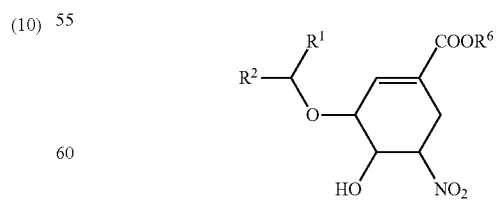
(1)

(wherein $R^1$, $R^2$ and $R^6$ are same or different and are each alkyl, aryl, substituted aryl, aralkyl, substituted aralkyl or aromatic heterocyclic group, and $R^1$ and $R^2$ are not methyl simultaneously)

In the present invention, $R^1$, $R^2$ and $R^6$ are alkyl, aryl, substituted aryl, aralkyl, substituted aralkyl or aromatic heterocyclic group.

Examples of alkyl groups usable are straight-chain, branched chain or cyclic alkyl groups having 1 to 8 carbon atoms, such as methyl, ethyl, n-propyl, isopropyl, cyclopropyl, n-butyl, sec-butyl, tert-butyl, cyclobutyl, n-pentyl, n-hexyl, n-heptyl and n-octyl. Preferable alkyl groups are straight-chain or branched chain alkyl groups having 1 to 4 carbon atoms. Ethyl is more preferable.

Examples of aryl groups are aryl groups having 6 to 10 carbon atoms, such as phenyl and naphthyl. Preferable is phenyl.

Examples of substituents of aryl groups having a substituent are alkyl having 1 to 8 carbon atoms, alkoxyl having 1 to 8 carbon atoms, halogen atom, hydroxyl, amino, nitro, cyano, carbonyl-containing groups represented by —$COR^b$ ($R^b$=$C_1$-$C_8$ alkyl, aryl, $C_1$-$C_8$ alkoxyl or aryloxy), sulfonyl, trifluoromethyl, etc.

Examples of aralkyl groups are aralkyl groups having 7 to 20 carbon atoms, such as benzyl, phenylethyl, phenylbutyl, naphthylmethyl and naphthylethyl. Preferable are benzyl and phenylethyl.

Examples of substituents of aralkyl groups are the same as substituents for aryl groups.

Examples of aromatic heterocyclic groups are pyridyl, pyrrol, furyl and thienyl.

The above nitro group-containing ether compound of the formula (1) can be prepared by subjecting a dihydroxyhexenoic acid ester of the formula (4c) to oxidative diol-cleavage reaction, and further subjecting the resulting compound to intramolecular nitroaldol reaction.

The above dihydroxyhexenoic acid ester of the formula (4c) can be, for example, prepared by using D-tartaric acid, mannnitol or arabinose as a starting material.

1. Following is a representative example of preparing compound (4c) using tartaric acid as a starting material.

D-tartaric acid is reacted with ketone to form a tartaric acid ester-pentanone acetal of the formula (5a). The acetal is hydrolysed with addition of an alkali metal hydroxide to obtain a monocarboxylic acid compound of the formula (5). The compound (5) is reacted with $BH_3$—S(dialkyl) to prepare a hydroxyester compound of the formula (4a). The compound (4a) is reacted with 3,4-dihydro-2H-pyran (DHP) and (+)camphor sulfonic acid (CSA) to obtain an ester compound of the formula (4b) wherein hydroxyl group is protected with a protective group $D^a$.

The compound (4b) is reacted with hydrogenated diisobutyl aluminum (DIBAL-H), further with ethyl acrylate and 1,4-diazabicyclo[2.2.2]octane(DABCO), and further with triethylamine, acetic anhydride and N-dimethylaminopyridine to obtain an acyloxy unsaturated ester compound of the formula (3b).

The compound (3b) is subjected to nitromethyllation with addition of nitromethane and an alkali metal hydroxide to obtain a nitroester compound of the formula (2b). The compound (2b) is deprotected with addition of hydrogen halogenate to obtain a hydroxynitroester compound of the formula (2a).

The compound (2a) is subjected to reductive acetal cleavage reaction with addition of, for example, $BH_3$-$SMe_2$ and $BF_3OEt_2$ to obtain a dihydroxyhexenoic acid ester of the formula (4c).

Specific examples of compound (4c) are
4-(1-ethylpropoxy)-5,6-dihydroxy-2-(2-nitroethyl)hex-2-enoic acid ethyl ester,
4-(1-ethylpropoxy)-5,6-dihydroxy-2-(2-nitroethyl)hex-2-enoic acid methyl ester,
4-cyclohexyloxy-5,6-dihydroxy-2-(2-nitroethyl)hex-2-enoic acid tert-butyl ester,
5,6-dihydroxy-2-(2-nitroethyl)-4-(1-phenylpentyloxy)hex-2-enoic acid benzyl ester and
5,6-dihydroxy-2-(2-nitroethyl)-4-(1-pyridine-2-ylpropoxy)hex-2-enoic acid ethyl ester.

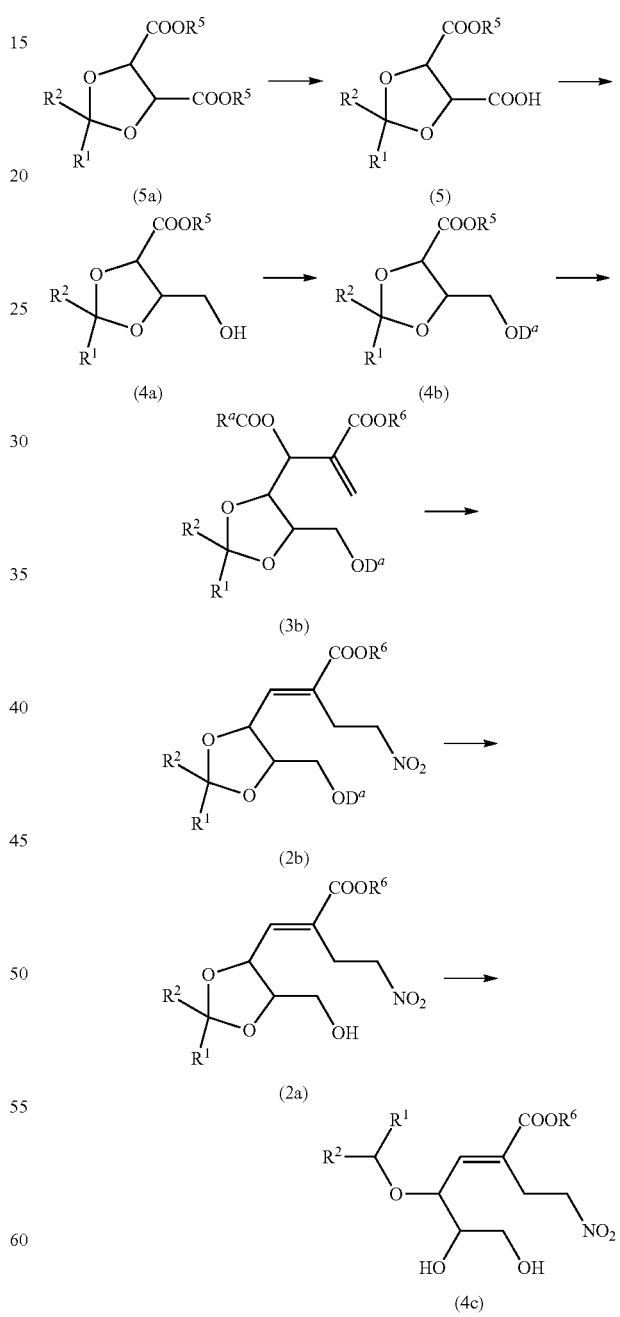

The method of preparing compound (4c) using tartaric acid as a starting material is described in detail in JP patent application No. 2009-162840, and a PCT application filed on Jun.

4, 2010 which has priorities of four Japanese applications including the above No. 2009-162840.

Namely, the above tartaric acid ester-pentanone acetal of the formula (5a) is a known compound and can be prepared by subjecting known tartaric acid to esterification and acetallization.

Specifically, D-tartaric acid is used in an amount of 0.1 to 10 equivalents per equivalent of a ketone.

Examples of ketones are those represented by $R^1COR^2$ ($R^1$ and $R^2$ are same as above). Specific examples of ketones are diethyl ketone, methyl octyl ketone, cyclohexanone, butyl phenyl ketone, benzyl methyl ketone and ethyl-2-pyridyl ketone.

Examples of solvents are ethers such as tetrahydrofuran (THF), alcohols such as ethanol (EtOH), esters such as ethyl acetate, hydrocarbons such as toluene and hexane, amides such as dimethyl formamide (DMF), dimethylsulfoxide (DMSO), acetonitrile, dichloromethane and dichloroethane. The solvent can be used in an amount of 1 to 200 times of the reactants. The reaction is preferably conducted at −78 to 100° C., more preferably at 0 to 100° C. for 1 to 24 hours.

The monocarboxylic acid (5) can be prepared by reacting the tartaric acid ester-pentanone acetal (5a) with potassium hydroxide.

Specifically, the tartaric acid ester-pentanone acetal is dissolved in a solvent and then reacted with potassium hydroxide. As potassium hydroxide, an aqueous solution of 0.1 to 10 N potassium hydroxide solution is preferably used. Potassium hydroxide is used in an amount of 1 to 10 equivalents per equivalent of the tartaric acid ester-pentanone acetal. Examples of solvents are ethers such as tetrahydrofuran (THF), alcohols such as ethanol (EtOH), esters such as ethyl acetate, hydrocarbons as toluene and hexane, amides such as dimethyl formamide an dimethylsulfoxide (DMSO), acetonitrile, dichloromethane and dichloroethane. The solvent can be used in an amount of 1 to 200 times of the reactants. The reaction is preferably conducted at −78 to 100° C., more preferably at 0 to 100° C. for 1 to 24 hours. After completion of reaction, the reaction mixture is neutralized with aqueous solution of 0.01 to 12 N of hydrochloric acid or the like.

The hydroxyester (4a) can be prepared by reacting the monocarboxylic acid (5) with $BH_3$—$SMe_2$.

Specifically, the monocarboxylic acid is dissolved in a solvent and then reacted with $BH_3$—$SMe_2$. $BH_3$—$SMe_2$ is used in an amount of 1 to 10 equivalents per equivalent of the monocarboxylic acid. Same solvents as above are used. The solvent can be used in an amount of 1 to 200 times of the reactants. The reaction is preferably conducted at −78 to 100° C., more preferably at 0 to 30° C. for 1 to 24 hours. The ester (4b) can be prepared by reacting the hydroxyester (4a) with 3,4-dihydro-2H-pyran (DHP) and (+)camphor sulfonic acid (CSA).

Specifically, the hydroxyester is dissolved in a solvent and then reacted with DHP and CSA. DHP is used in an amount of 1 to 10 equivalents per equivalent of the hydroxyester. CSA is used in an amount of 1 to 10 equivalents per equivalent of the hydroxyester. Same solvents as above are used. The solvent can be used in an amount of 1 to 200 times of the reactants. The reaction is preferably conducted at −78 to 100° C., more preferably at 0 to 30° C. for 1 to 24 hours. After completion of reaction, the reaction mixture is neutralized with aqueous solution of saturated $NaHCO_3$ or the like.

Examples of protective groups of hydroxyl represented by $D^a$ are oxyalkyl group having 1 to 10 carbon atoms, substituted or unsubstituted aryl group having 6 to 10 carbon atoms, substituted or unsubstituted aralkyl group having 7 to 14 carbon atoms, and silyl group having alkyl group of 1 to 8 carbon atoms or aryl group.

Examples of oxyalkyl groups having 1 to 10 carbon atoms are straight-chain, branched chain or cyclic oxyalkyl having 1 to 8 carbon atoms such as methoxymethyl, ethoxymethyl and tetrahydropyranyl.

Examples of substituted or unsubstituted aryl groups having 6 to 10 carbon atoms are phenyl, those having alkyl substituent such as tolyl, those having heteroatom in side chain substituent, and those having heteroatom in aryl ring.

Examples of substituted or unsubstituted aralkyl groups having 7 to 14 carbon atoms are branched chain or cyclic alkyl which is substituted by aryl group such as phenyl and tolyl.

Further, those having heteroatom in substituent, and those having heteroatom in aryl ring are included.

Examples of silyl groups having alkyl group of 1 to 8 carbon atoms or aryl group are trimethylsilyl, triethylsilyl, t-butyldimethylsilyl, triisopropylsilyl and triphenylsilyl.

Specific examples of alkyl, aryl and aralkyl groups are the same as those shown in the above $R^1$ and $R^2$.

Examples of protective groups are preferably straight-chain or branched chain oxyalkyl groups having 1 to 10 carbon atoms. More preferable is tetrahydropyranyl.

In preparing acyloxy unsaturated ester from the ester (4b), the ester (4b) is reacted with hydrogenated diisobutyl aluminum (DIBAL-H), then the resulting product is reacted with ethyl acrylate and 1,4-diazabicyclo[2,2,2]octane (DABCO). Further, the resulting product is reacted with triethylamine, acetic anhydride and N,N-dimethylaminopyridine to obtain an acetoxy unsaturated ester.

Specifically, the ester (4b) is dissolved in a solvent and then reacted with DIBAL-H. DIBAL-H is used in an amount of 1 to 10 equivalents per equivalent of the ester (4b). Same solvents as above are used. The solvent can be used in an amount of 1 to 200 times of the reactants. The reaction is preferably conducted at −78 to 100° C., more preferably at 0 to 30° C. for 1 to 24 hours.

Then, the resulting product is reacted with ethyl acrylate and DABCO. Ethyl acrylate can be used in an amount of 1 to 100 equivalents per equivalent of the ester (4b). DABCO can be used in an amount of 1 to 100 equivalents per equivalent of the ester (4b). The reaction is preferably conducted at −78 to 100° C., more preferably at 0 to 30° C. for 1 to 24 hours.

Further, the resulting product is reacted with triethylamine, acetic anhydride and N,N-dimethylaminopyridine. Triethylamine can be used in an amount of 1 to 10 equivalents per equivalent of the ester (4b). Acetic anhydride can be used in an amount of 1 to 10 equivalents per equivalent of the ester (4b). N,N-Dimethylamino-pyridine can be used in an amount of 1 to 10 equivalents per equivalent of the ester (4b). The reaction is preferably conducted at −78 to 100° C., more preferably at 0 to 30° C. for 1 to 24 hours.

The nitroester (2b) can be prepared by reacting the acyloxy unsaturated ester (3b) with nitromethane and potassium hydroxide.

Specifically, nitromethane is dissolved in a solvent and then reacted with potassium hydroxide. To the reaction mixture was added the acyloxy unsaturated ester dissolved in a solvent for reaction. Nitromethane can be used in an amount of 1 to 100 equivalents per equivalent of the acyloxy unsaturated ester. Potassium hydroxide can be used in an amount of 0.1 to 100 equivalents per equivalent of the acyloxy unsaturated ester. Same solvents as above are used. The solvent can be used in an amount of 1 to 200 times of the reactants. The reaction is preferably conducted at −78 to 100° C., more preferably at 0 to 30° C. for 1 to 24 hours. After completion of reaction, the reaction mixture is neutralized with aqueous solution of saturated ammonium chloride or the like.

The hydroxynitroester (2a) can be prepared by reacting the nitroester (2b) with, for example, HCl.

Specifically, the nitroester is dissolved in a solvent and then reacted with HCl. As HCl, an aqueous solution of 0.01 to 12 N HCl solution is preferably used. HCl is used in an amount of 0.1 to 100 equivalents per equivalent of the nitroester. Same solvents as above are used. The solvent can be used in an amount of 1 to 200 times of the reactants. The reaction is preferably conducted at −78 to 100° C., more preferably at 0 to 30° C. for 1 to 24 hours. After completion of reaction, the reaction mixture is neutralized with aqueous solution of saturated $NaHCO_3$ or the like.

The dihydroxyhexenoic acid ester of the formula (1) can be prepared by reacting the hydroxynitroester of the formula (2a) with, for example, $BH_3SMe_2$ and $BF_3OEt_2$ to conduct reductive acetal-cleavage reaction.

Specifically, the hydroxynitroester is dissolved in a solvent and then reacted with $BH_3SMe_2$. $BH_3SMe_2$ is used in an amount of 1 to 10 equivalents per equivalent of the hydroxynitroester. Same solvents as above are used. The solvent can be used in an amount of 1 to 200 times of the reactants. The reaction is preferably conducted at −78 to 100° C., more preferably at 0 to 30° C. for 1 to 24 hours. Thereafter, $BF_3OEt_2$ is added to the reaction solution and the reaction is conducted. $BF_3OEt_2$ is used in an amount of 0.1 to 100 equivalents per equivalent of the hydroxynitroester (2a). The reaction is preferably conducted at −78 to 100° C., more preferably at 0 to 30° C. for 1 to 24 hours.

After completion of reaction, each of the above reaction products can be isolated and purified by the methods usually conducted in the isolation and purification of the organic compounds. For example, after completion of reaction, the reaction product can be extracted with a solvent such as hexane or like aliphatic hydrocarbon, toluene or like aromatic hydrocarbon, dichloromethane or like halogenated hydrocarbon, diethyl ether, diisopropyl ether or like ether. The extract is concentrated and the concentrate is purified by distillation, silica gel column chromatography, or the like.

Specific examples of compound (5) are
2,2-diethyl-[1,3]dioxolane-4,5-dicarboxylic acid monomethyl ester,
2-methyl-2-octyl-[1,3]dioxolane-4,5-dicarboxylic acid monobutyl ester,
1,4-dioxaspiro[4,5]decane-2,3-dicarboxylic acid monoocthyl ester,
2-butyl-2-phenyl-[1,3]dioxolane-4,5-dicarboxylic acid monobenzyl ester,
2-benzyl-2-methyl-[1,3]dioxolane-4,5-dicarboxylic acid monopyridine-2-ylmethyl ester and
2-ethyl-2-pyridine-2-yl-[1,3]dioxolane-4,5-dicarboxylic acid monofuran-2-ylmethyl ester.

Specific examples of compound (4a) are
2,2-diethyl-5-hydroxymethyl-[1,3]dioxolane-4-carboxylic acid methyl ester,
5-hydroxymethyl-2-methyl-2-octyl-[1,3]dioxolane-4-carboxylic acid butyl ester,
3-hydroxymethyl-1,4-dioxaspiro[4,5]decane-2-carboxylic acid octyl ester,
2-butyl-5-hydroxymethyl-2-phenyl-[1,3]dioxolane-4-carboxylic acid benzyl ester,
2-benzyl-5-hydroxymethyl-2-methyl-[1,3]dioxolane-4-carboxylic acid pyridine-2-ylmethyl ester and
2-ethyl-5-hydroxymethyl-2-pyridine-2-yl-[1,3]dioxolane-4-carboxylic acid furan-2-ylmethyl ester.

Specific examples of compound (4b) are
2,2-diethyl-5-(tetahydropyran-2-yloxymethyl)-[1,3]dioxolane-4-carboxylic acid methyl ester,
2,2-diethyl-5-(4-methoxybenzyloxymethyl)-[1,3]dioxolane-4-carboxylic acid methyl ester,
5-(tert-butyldimethylsiloxymethyl)-2-methyl-2-octyl-[1,3]dioxolane-4-carboxylic acid methyl ester,
3-methoxymethoxymethyl-1,4-dioxaspiro[4,5]decane-2-carboxylic acid octyl ester,
2-butyl-2-phenyl-5-(tetahydropyran-2-yloxymethyl)-[1,3]dioxolane-4-carboxylic acid benzyl ester,
2-benzyl-2-methyl-5-(tetahydropyran-2-yloxymethyl)-[1,3]dioxolane-4-pyridine-2-ylmethyl ester and
2-ethyl-5-methoxymethoxymethyl-2-pyridine-2-yl-[1,3]dioxolane-4-carboxylic acid furan-2-ylmethyl ester.

Specific examples of compound (3b) are
2-[acetoxy-[2,2-diethyl-5-(tetahydropyran-2-yloxymethyl)-[1,3]dioxolane-4-yl]methyl] acrylic acid ethyl ester,
2-{acetoxy-[2,2-diethyl-5-(4-methoxybenzyloxymethyl)-[1,3]dioxolane-4-yl]methyl}acrylic acid methyl ester,
2-{acetoxy-[5-(tert-butyldimethylsiloxymethyl)-2,2-diethyl-[1,3]dioxolane-4-yl]methyl}acrylic acid tert-butyl ester,
2-[acetoxy-(3-methoxymethoxymethyl-1,4-dioxaspiro[4,5]deca-2-yl) methyl] acrylic acid tert-butyl ester,
2-{acetoxy-[2-butyl-2-phenyl-5-(tetahydropyran-2-yloxymethyl)-[1,3]dioxolane-4-yl]methyl}acrylic acid benzyl ester,
2-{acetoxy-[2-benzyl-2-methyl-5-(tetahydropyran-2-yloxymethyl)-[1,3]dioxolane-4-yl]methyl}acrylic acid ethyl ester and
2-[acetoxy-(2-ethyl-5-methoxymethoxymethyl-2-pyridine-2-yl-[1,3]dioxolane-4-yl)methyl]acrylic acid methyl ester.

Specific examples of compound (2b) are
3-[2,2-diethyl-5-(tetahydropyran-2-yloxymethyl)-[1,3]dioxolane-4-yl]-2-(2-nitroethyl) acrylic acid ethyl ester,
3-[2,2-diethyl-5-(4-methoxymethoxymethyl)-[1,3]dioxolane-4-yl]-2-(2-nitroethyl) acrylic acid methyl ester,
3-[5-(tert-butyldimethylsiloxymethyl)-2,2-diethyl-[1,3]dioxolane-4-yl]-2-(2-nitroethyl) acrylic acid tert-butyl ester,
3-(3-methoxymethoxymethyl-dioxaspiro[4,5]deca-2-yl)-2-(2-nitroethyl) acrylic acid tert-butyl ester,
3-[2-butyl-2-phenyl-5-(tetahydropyran-2-yloxymethyl)-[1,3]dioxolane-4-yl]-2-(2-nitroethyl) acrylic acid benzyl ester and
3-[2-benzyl-2-methyl-5-(tetahydropyran-2-yloxymethyl)-[1,3]dioxolane-4-yl]-2-(2-nitroethyl) acrylic acid ethyl ester.

Specific examples of compound (2a) are
3-[2,2-diethyl-5-hydroxymethyl-[1,3]dioxolane-4-yl]-2-(2-nitroethyl) acrylic acid ethyl ester,
3-[2,2-diethyl-5-hydroxymethyl-[1,3]dioxolane-4-yl]-2-(2-nitroethyl) acrylic acid methyl ester,
3-(3-hydroxymethyl-1,4-dioxaspiro[4,5]deca-2-yl)-2-(2-nitroethyl) acrylic acid tert-butyl ester,
3-(2-butyl-5-hydroxymethyl-2-phenyl-[1,3]dioxolane-4-yl)-2-(2-nitroethyl) acrylic acid benzyl ester,
3-(2-ethyl-5-hydroxymethyl-2-pyridine-2-yl-[1,3]dioxolane-4-yl)-2-(2-nitroethyl) acrylic acid tert-butyl ester and
3-(2-benzyl-5-hydroxymethyl-2-methyl-[1,3]dioxolane-4-yl)-2-(2-nitroethyl) acrylic acid ethyl ester.

2. Following is a representative example of preparing compound (4c) using mannitol as a starting material.

D-(−)-mannitol which is a known compound is reacted with 3-pentanone, ethyl orthoformate and DL-10-camphor sulfonic acid. The resulting product is reacted with triethylamine (amine compound) to obtain a mannitol triacetal compound of the formula (11). The compound (11) is reacted with ethylene glycol and methane sulfonic acid, and then the resulting product is reacted with perhalogenic acid to prepare an aldehyde compound of the formula (10). The compound (10) is reacted with ethyl acrylate and 1,4-diazabicyclo[2.2.2]octane (DABCO). The resulting product is reacted with triethylamine (amine compound) and acetic anhydride to obtain an acyloxy unsaturated ester compound of the formula (9). The compound (9) is reacted with nitromethane and alkali metal hydroxide, and then with hydrogen halogenate to perform nitromethylation to prepare a nitroester compound of the formula (8). The compound (8) is reacted with DL-10-camphor sulfonic acid, and then with triethylamine (amine compound) to obtain a nitrodiol compound of the formula (7). The compound (7) is subjected to diol-cleavage reaction to prepare a formyl nitroester compound of the formula (6). The compound (6) is reduced to obtain a hydroxy nitroester compound of the formula (2a). The compound (2a) is subjected to reductive acetal-cleavage reaction by reacting with, for example, $BH_3SMe_2$ and $BF_3OEt_2$ to obtain a dihydroxyhexenoic acid ester of the formula (4c).

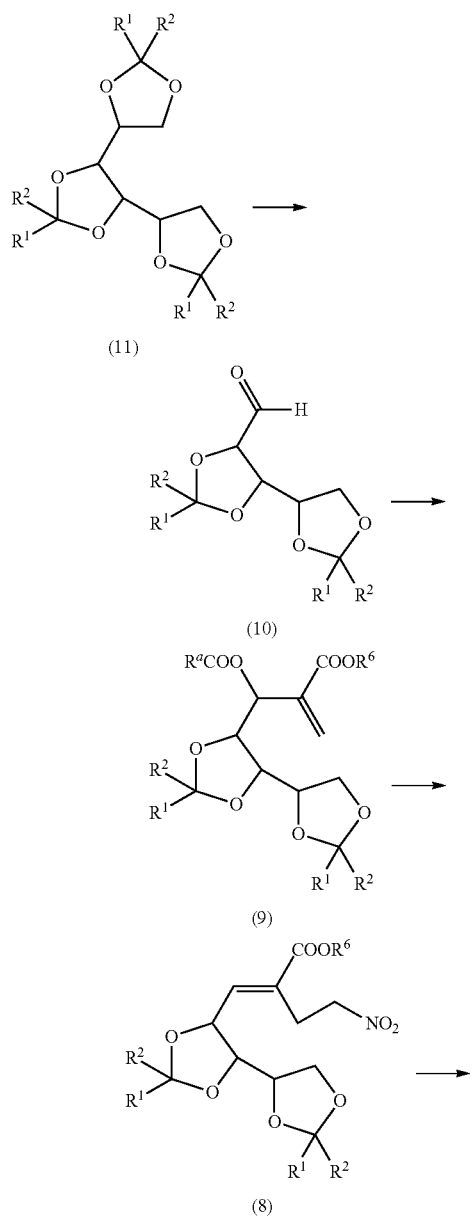

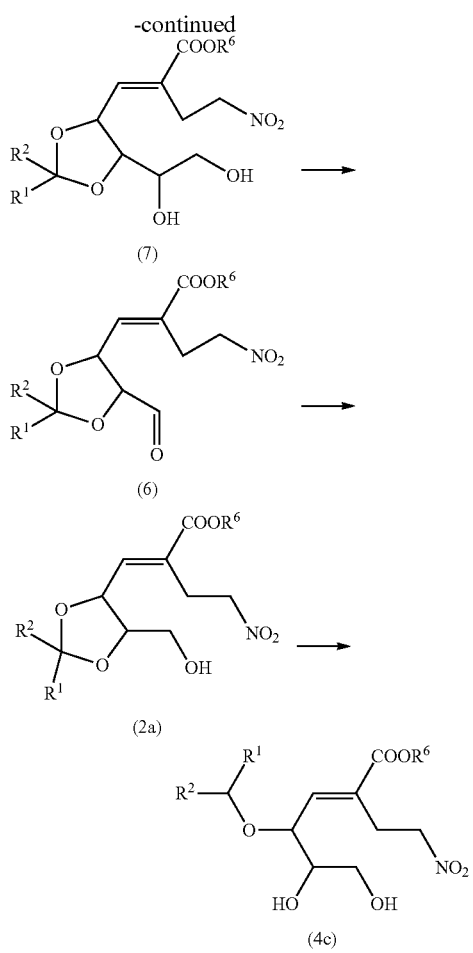

The method of preparing compound (4c) using mannitol as a starting material is described in detail in JP patent application No. 2009-138720, and the above PCT application filed on Jun. 4, 2010.

Namely, for preparing a mannitol triacetal compound from D-(−)-mannitol, 3-pentanone, ethyl orthoformate and DL-10-camphor sulfonic acid are reacted. Then, the resulting product is reacted with triethylamine to obtain a mannitol triacetal compound of the formula (11).

Specifically, 3-pentanone is dissolved in a solvent and then reacted with ethyl orthoformate and DL-10-camphor sulfonic acid. 3-Pentanone can be used in an amount of 3 to 10 equivalents per equivalent of D-(−)-mannitol. Ethyl orthoformate can be used in an amount of 3 to 10 equivalents per equivalent of D-(−)-mannitol. DL-10-camphor sulfonic acid can be used in an amount of 0.1 to 1 equivalent per equivalent of D-(−)-mannitol. Examples of solvents are ethers such as tetrahydrofuran (THF), alcohols such as ethanol, esters such as ethyl acetate, hydrocarbones such as toluene and hexane, amides such as dimethyl formamide (DMF), dimethylsulfoxide (DMSO), acetonitrile, dichloromethane and dichloroethane. The solvent can be used in an amount of 1 to 200 times of the reactants. The reaction is preferably conducted at 0 to 100° C., more preferably at 0 to 60° C. for 1 to 24 hours.

Thereafter, triethylamine is added to the reaction solution for reaction. Triethylamine can be used in an amount of 0.1 to 2 equivalents per equivalent of D-(−)-mannitol. The reaction is preferably conducted at 0 to 100° C., more preferably at 0 to 40° C. for 1 to 24 hours.

For preparing an aldehyde compound (10) from the mannitol triacetal compound (11), the mannitol triacetal compound is reacted with ethylene glycol and methane sulfonic acid, and then the resulting product is reacted with $HIO_4$ to prepare the aldehyde compound of the formula (10).

Specifically, the mannitol triacetal compound is dissolved in a solvent and then reacted with ethylene glycol and methane sulfonic acid. Ethylene glycol can be used in an amount of 0.1 to 3 equivalents per equivalent of the mannitol triacetal compound. Methane sulfonic acid can be used in an amount of 0.1 to 1 equivalent per equivalent of the mannitol triacetal compound. Same solvents as above are used. The solvent can be used in an amount of 1 to 200 times of the reactants. The reaction is preferably conducted at −78 to 100° C., more preferably at 0 to 60° C. for 1 to 24 hours.

Thereafter, $HIO_4$ is added to the reaction solution for reaction. $HIO_4$ is usable in hydrate thereof such as $HIO_4 \cdot 2H_2O$ and can be used in an amount of 0.1 to 2 equivalents per equivalent of the mannitol triacetal compound. After completion of reaction, the reaction mixture is neutralized with aqueous solution of saturated $NaHCO_3$ or the like.

For preparing an acyloxy unsaturated ester compound of the formula (9) from the aldehyde compound (10), the aldehyde compound is reacted with ethyl acrylate and 1,4-diazabicyclo[2.2.2]octane (DABCO), and then the resulting product is reacted with triethylamine and acetic anhydride to prepare the acyloxy unsaturated ester compound (9).

Specifically, the aldehyde compound is reacted with ethyl acrylate and DABCO. Ethyl acrylate can be used in an amount of 1 to 100 equivalents per equivalent of the aldehyde compound. DABCO can be used in an amount of 0.1 to 100 equivalents per equivalent of the aldehyde compound. Solvent is not used or same solvents as above are used. The solvent can be used in an amount of 1 to 200 times of the reactants. The reaction is preferably conducted at −78 to 100° C., more preferably at 0 to 30° C. for 1 to 24 hours.

Thereafter, triethylamine and acetic anhydride are added to the reaction solution for reaction. Triethylamine can be used in an amount of 1 to 10 equivalents per equivalent of the aldehyde compound. Acetic anhydride can be used in an amount of 1 to 10 equivalents per equivalent of the aldehyde compound. The reaction is preferably conducted at −78 to 100° C., more preferably at 0 to 30° C. for 1 to 24 hours.

The nitroester compound of the formula (8) can be prepared by reacting the acyloxy unsaturated ester compound of the formula (9) with nitromethane and potassium hydroxide.

Specifically, the acyloxy unsaturated ester compound is dissolved in a solvent and then a solution of potassium hydroxide and nitromethane in a solvent is added thereto. Nitromethane can be used in an amount of 1 to 100 equivalents per equivalent of the acyloxy unsaturated ester compound. Potassium hydroxide can be used in an amount of 1 to 10 equivalents per equivalent of the acyloxy unsaturated ester compound. Same solvents as above are used. The solvent can be used in an amount of 1 to 200 times of the reactants. The reaction is preferably conducted at −78 to 100° C., more preferably at 0 to 30° C. for 1 to 24 hours. After completion of reaction, the reaction mixture is neutralized with aqueous solution of 0.01 to 12 N hydrochloric acid or the like.

The nitrodiol compound of the formula (7) can be prepared by reacting the nitroester compound of the formula (8) with DL-10-camphor sulfonic acid and then with triethylamine.

Specifically, the nitroester compound is dissolved in a solvent and then reacted with DL-10-camphor sulfonic acid. DL-10-Camphor sulfonic acid can be used in an amount of 0.1 to 10 equivalents per equivalent of the nitroester compound. Same solvents as above are used. The solvent can be used in an amount of 1 to 200 times of the reactants. The reaction is preferably conducted at −78 to 100° C., more preferably at 0 to 30° C. for 1 to 24 hours. After completion of reaction, the reaction mixture is neutralized with triethylamine. Triethylamine can be used in an amount of 0.01 to 20 equivalents per equivalent of the nitroester compound.

The formyl nitroester compound of the formula (6) can be prepared by reacting the nitrodiol compound of the formula (7) with $HIO_4$.

Specifically, the nitrodiol compound is dissolved in a solvent and then reacted with $HIO_4$. $HIO_4$ is usable in hydrate thereof such as $HIO_4 \cdot 2H_2O$ and can be used in an amount of 0.1 to 10 equivalents per equivalent of the nitrodiol compound. Same solvents as above are used. The solvent can be used in an amount of 1 to 200 times of the reactants. The reaction is preferably conducted at −78 to 100° C., more preferably at 0 to 30° C. for 1 to 24 hours. After completion of reaction, the reaction mixture is neutralized with aqueous solution of saturated $NaHCO_3$ or the like.

The hydroxy nitroester compound of the formula (2a) can be prepared by reacting the formyl nitroester compound of the formula (6) with hydride reducing agent such as $NaBH_4$ and $BH_3$.

Specifically, the formyl nitroester compound is dissolved in a solvent and then reacted with hydride reducing agent such as $NaBH_4 \bullet$ and $BH_3$. Hydride reducing agent can be used in an amount of 0.1 to 10 equivalents per equivalent of the formyl nitroester compound (6). Same solvents as above are used. The solvent can be used in an amount of 1 to 200 times of the reactants. The reaction is preferably conducted at −78 to 100° C., more preferably at 0 to 30° C. for 1 to 24 hours. After completion of reaction, the reaction mixture is neutralized with diluted hydrochloric acid or the like.

As mentioned above, the dihydroxyhexenoic acid ester of the formula (1) can be prepared by reacting the hydroxynitroester of the formula (2a) with, for example, $BH_3SMe_2$ and $BF_3OEt_2$ to conduct reductive acetal-cleavage reaction.

After completion of reaction, each of the above reaction products can be isolated and purified by the methods usually conducted in the isolation and purification of the organic compounds. For example, after completion of reaction, the reaction product can be extracted with a solvent such as hexane or like aliphatic hydrocarbon, toluene or like aromatic hydrocarbon, dichloromethane or like halogenated hydrocarbon, diethyl ether, diisopropyl ether or like ether. The extract is concentrated and the concentrate is purified by distillation, silica gel column chromatography, or the like.

Specific examples of compound (11) are mannitol-tri(3-pentanone)acetal, mannitol-tri(cyclohexanone)acetal, mannitol-tri(butyl phenyl ketone)acetal, mannitol-tri(ethyl-2-pyridyl ketone)acetal and mannitol-tri(benzyl methyl ketone)acetal.

Specific examples of compound (10) are 2,2,2', 2'-tetraethyl-[4,4']bis[[1,3]dioxolanyl]-5-carboaldehyde,

[2,2']bis[1,4-dioxaspiro[4,5]decyl]-3-carboaldehyde, 2,2'-dibutyl-2,2'-diphenyl-[4,4']bis[[1,3]dioxolanyl]-5-carboaldehyde, 2,2'-diethyl-2,2'-dipyridine-2-yl-[4,4']bis[[1,3]dioxolanyl]-5-carboaldehyde and 2,2'-dibenzyl-2,2'-dimethyl-[4,4']bis[[1,3]dioxolanyl]-6-carboaldehyde.

Specific examples of compound (9) are
2-[acetoxy-(2,2,2',2'-tetraethyl-[4,4']bis[[1,3]dioxolanyl]-5-yl)-methyl]-acrylic ethyl ester,
2-[acetoxy-(2,2,2',2'-tetraethyl-[4,4']bis[[1,3]dioxolanyl]-5-yl)-methyl]-acrylic methyl ester,
2-[acetoxy-([2,2']bis[[1,4-dioxaspiro[4,5]decyl]-3-yl)-methyl]-acrylic ethyl ester,
2-[acetoxy-(2,2'-dibutyl-2,2'-diphenyl-[4,4']bis[[1,3]dioxolanyl]-5-yl)-methyl]-acrylic benzyl ester,
2-[acetoxy-(2,2'-diethyl-2,2'-dipyridine-2-yl-[4,4']bis[[1,3]dioxolanyl]-5-yl)-methyl]-acrylic methyl ester and
2-[acetoxy-(2,2'-dibenzyl-2,2'-dimethyl-[4,4']bis[[1,3]dioxolanyl]-5-yl)-methyl]-acrylic tert-butyl ester.

Specific examples of compound (8) are
2-(2-nitroethyl)-3-(2,2,2',2'-tetraethyl-[4,4']bis[[1,3]dioxolanyl]-5-yl)-acrylic ethyl ester,
2-(2-nitroethyl)-3-(2,2,2',2'-tetraethyl-[4,4']bis[[1,3]dioxolanyl]-5-yl)-acrylic methyl ester,
3-([2,2']bis[1,4-dioxaspiro[4.5]decyl]-3-yl)-2-(2-nitroethyl)-acrylic ethyl ester,
3-(2,2'-dibutyl-2,2'-diphenyl-[4,4']bis[[1,3]dioxolanyl]-5-yl)-2-(2-nitroethyl)-acrylic benzyl ester,
3-(2,2'-diethyl-2,2'-dipyridine-2-yl-[4,4']bis[[1,3]dioxolanyl]-5-yl)-2-(2-nitroethyl)-acrylic methyl ester and
3-(2,2'-dibenzyl-2,2'-dimethyl-[4,4']bis[[1,3]dioxolanyl]-5-yl)-2-(2-nitroethyl)-acrylic tert-butyl ester.

Specific examples of compound (7) are
3-[5-(1,2-dihydroxyethyl)-2,2-diethyl-[1,3]dioxolane-4-yl]-2-(2-nitroethyl)-acrylic ethyl ester,
3-[5-(1,2-dihydroxyethyl)-2,2-diethyl-[1,3]dioxolane-4-yl]-2-(2-nitroethyl)-acrylic methyl ester,
3-[3-(1,2-dihydroxyethyl)-1,4-dioxaspiro[4,5]deca-2-yl]-2-(2-nitroethyl)-acrylic ethyl ester,
3-[2-butyl-5-(1,2-dihydroxyethyl)-2-phenyl-[1,3]dioxolane-4-yl]-2-(2-nitroethyl)-acrylic benzyl ester,
3-[5-(1,2-dihydroxyethyl)-2-ethyl-2-pyridine-2-yl-[1,3]dioxolane-4-yl]-2-(2-nitroethyl)-acrylic methyl ester and
3-[2-benzyl-5-(1,2-dihydroxyethyl)-2-methyl-[1,3]dioxolane-4-yl]-2-(2-nitroethyl)-acrylic tert-butyl ester.

Specific examples of compound (6) are
3-(2,2-diethyl-5-formyl-[1,3]dioxolane-4-yl]-2-(2-nitroethyl)-acrylic ethyl ester,
3-(2,2-diethyl-5-formyl-[1,3]dioxolane-4-yl)-2-(2-nitroethyl)-acrylic methyl ester,
3-(3-formyl-1,4-dioxaspiro[4,5]deca-2-yl)-2-(2-nitroethyl)-acrylic ethyl ester,
3-(2-butyl-5-formyl-2-phenyl-[1,3]dioxolane-4-yl)-2-(2-nitroethyl)-acrylic benzyl ester,
3-(2-ethyl-5-formyl-2-pyridine-2-yl-[1,3]dioxolane-4-yl)-2-(2-nitroethyl)-acrylic methyl ester and
acrylic 3-(2-benzyl-5-formyl-2-methyl-[1,3]dioxolane-4-yl)-2-(2-nitroethyl)-acrylic tert-butyl ester.

3. Following is a representative example of preparing compound (4c) using arabinose as a starting material.

Pentose is reacted with ketone and/or acetal compound of the formula (14c) to obtain a pentose acetal compound of the formula (14). The compound (14) is subjected to diol-cleavage reaction to prepare a formyl dioxolane compound of the formula (13). An acyloxy unsaturated ester compound (12) is prepared by subjecting acrylic ester to addition reaction and acylation reaction to compound (13). A hydroxy nitroester compound of the formula (2a) is prepared by subjecting nitromethylation to compound (12). The compound (2a) is subjected to reductive acetal-cleavage reaction to obtain a dihydroxyhexenoic acid ester of the formula (4c).

The method of preparing compound (4c) using arabinose as a starting material is described in detail in JP patent application No. 2009-204883, and the above PCT application filed on Jun. 4, 2010.

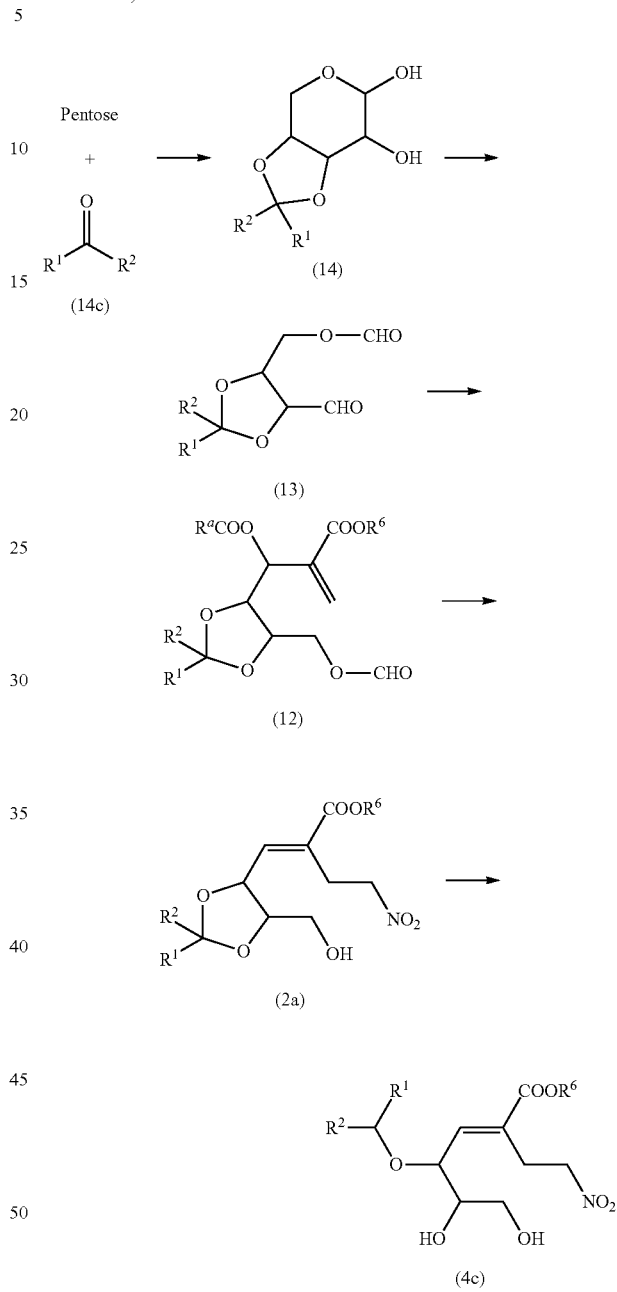

As a pentose is usable at least one aldose selected from among ribose, lyxose, xylose and arabinose. Preferable pentose are D-arabinose of the formula (14a) or (14b).

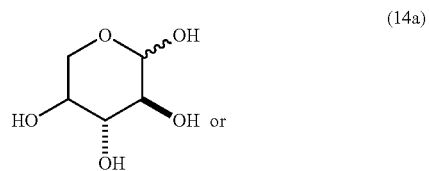

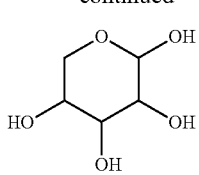
(14b)

Examples of ketones of the formula (14c) are acetone, methyl ethyl ketone, diethyl ketone, methyl propyl ketone, methyl isobutyl ketone, methyl phenyl ketone, ethyl phenyl ketone, benzophenone and methyl benzyl ketone. Examples of acetal derivatives of ketone are dimethyl acetal, methyl ethyl acetal, diethyl acetal, methyl propyl acetal, di-n-propyl acetal, diisopropyl acetal and methyl butyl acetal. Ketone and acetal thereof are usable singly or in at least two of them conjointly.

A pentose acetal compound of the formula (14) can be prepared by reacting pentose with ketone of the formula (14c) or acetal derivative thereof.

Specifically, diethyl ketone and/or acetal derivative thereof is used in an amount of 1 to 10 equivalents per equivalent of D-arabinose. Examples of solvents are ethers such as tetrahydrofuran (THF), alcohols such as ethanol (EtOH), esters such as ethyl acetate, hydrocarbons such as toluene and hexane, amides such as dimethyl formamide (DMF), dimethylsulfoxide (DMSO), acetonitrile, dichloromethane and dichloroethane. The solvent can be used in an amount of 1 to 200 times of the reactants. The reaction is preferably conducted at −78 to 100° C., more preferably at 0 to 100° C. for 1 to 24 hours.

The pentose acetal compound of the formula (14) is subjected to diol-cleavage reaction to prepare a formyl dioxolane compound of the formula (13).

Specifically, the pentose acetal compound is dissolved in a solvent and then reacted with periodic acid compound such as $KIO_4$ or $HIO_4 \cdot 2H_2O$ (hydrate). Periodic acid compound can be used in an amount of 0.1 to 10 equivalents per equivalent of the pentose acetal compound. Same solvents as above are used. The solvent can be used in an amount of 1 to 200 times of the reactants. The reaction is preferably conducted at −78 to 100° C., more preferably at 0 to 30° C. for 1 to 24 hours.

The acyloxy unsaturated ester compound (12) is prepared by subjecting acrylic ester to addition reaction and acylation reaction to the formyl dioxolane compound (13). Examples of acrylic esters are those represented by $CH_2=CHCOOR^5$ ($R^5$ is same as above). Specific examples are methyl acrylate, ethyl acrylate, butyl acrylate, heptyl acrylate, octyl acrylate, phenyl acrylate, naphthyl acrylate, and benzyl acrylate.

For example, ethyl acrylate and DABCO are added to the formyl dioxolane compound (13). Ethyl acrylate can be used in an amount of 1 to 100 equivalents per equivalent of the formyl dioxolane compound. DABCO can be used in an amount of 1 to 100 equivalents per equivalent of the formyl dioxolane compound. The reaction is preferably conducted at −78 to 100° C., more preferably at 0 to 30° C. for 1 to 24 hours. Further, to the reaction product are added triethylamine, acetic anhydride and N,N-dimethylaminopyridine. Triethylamine can be used in an amount of 1 to 10 equivalents per equivalent of the formyl dioxolane compound. Acetic anhydride can be used in an amount of 1 to 10 equivalents per equivalent of the reaction product. N,N-Dimethylaminopyridine can be used in an amount of 1 to 10 equivalents per equivalent of the formyl dioxolane compound. The reaction is preferably conducted at −78 to 100° C., more preferably at 0 to 30° C. for 1 to 24 hours.

A hydroxy nitroester compound of the formula (2a) is prepared by reacting the acyloxy unsaturated ester compound (12) with nitromethane and potassium hydroxide.

Specifically, nitromethane is dissolved in a solvent and then reacted with potassium hydroxide. Then, to the reaction solution is added a solution of the acyloxy unsaturated ester compound in a solvent. Nitromethane can be used in an amount of 1 to 100 equivalents per equivalent of the acyloxy unsaturated ester compound. Potassium hydroxide can be used in an amount of 0.1 to 100 equivalents per equivalent of the acyloxy unsaturated ester compound. Same solvents as above are used. The solvent can be used in an amount of 1 to 200 times of the reactants. The reaction is preferably conducted at −78 to 100° C., more preferably at 0 to 30° C. for 1 to 24 hours. After completion of reaction, the reaction mixture is neutralized with aqueous solution of saturated ammonium chloride or the like.

The compound (2a) is subjected to reductive acetal cleavage reaction with addition of, for example, $BH_3—SMe_2$ and $BF_3OEt_2$ to obtain the dihydroxyhexenoic acid ester of the formula (1).

After completion of reaction, each of the above reaction products can be isolated and purified by the methods usually conducted in the isolation and purification of the organic compounds. For example, after completion of reaction, the reaction product can be extracted with a solvent such as hexane or like aliphatic hydrocarbon, toluene or like aromatic hydrocarbon, dichloromethane or like halogenated hydrocarbon, diethyl ether, diisopropyl ether or like ether. The extract is concentrated and the concentrate is purified by distillation, silica gel column chromatography, or the like.

Specific examples of compound (14) are
2,2-diethyltetrahydro-[1,3]dioxolo[4,5-c]pyran-6,7-diol,
2-methyl-2-octyltetrahydro-[1,3]dioxolo[4,5-c]pyran-6,7-diol,
2-butyl-2-phenyltetrahydro-[1,3]dioxolo[4,5-c]pyran-6,7-diol,
2-benzyl-2-methyltetrahydro-[1,3]dioxolo[4,5-c]pyran-6,7-diol and
2-ethyl-2-pyridine-2-yltetrahydro-[1,3]dioxolo[4,5-c]pyran-6,7-diol Specific examples of compound (13) are
formic acid 2,2-diethyl-5-formyl-[1,3]dioxolan-4-ylmethyl ester,
formic acid 2-methyl-2-octyl-5-formyl-[1,3]dioxolan-4-ylmethyl ester,
formic acid 2-butyl-2-phenyl-5-formyl-[1,3]dioxolan-4-ylmethyl ester,
formic acid 2-benzyl-2-methyl-5-formyl-[1,3]dioxolan-4-ylmethyl ester and
formic acid 2-ethyl-2-pyridine-2-yl-5-formyl-[1,3]dioxolan-4-ylmethyl ester.

Specific examples of compound (12) are
2-[acetoxy-(2,2-diethyl-5-formyloxymethyl-[1,3]dioxolan-4-yl) methyl]acrylic acid ethyl ester,
2-[acetoxy-(2-methyl-2-octyl-5-formyloxymethyl-[1,3]dioxolan-4-yl) methyl]acrylic acid methyl ester,
2-[acetoxy-(2-butyl-2-phenyl-5-formyloxymethyl-[1,3]dioxolan-4-yl) methyl]acrylic acid benzyl ester,
2-[acetoxy-(2-benzyl-2-methyl-5-formyloxymethyl-[1,3]dioxolan-4-yl) methyl]acrylic acid ethyl ester and
2-[acetoxy-(2-methyl-2-pyridine-2-yl-5-formyloxymethyl-[1,3]dioxolan-4-yl)methyl]acrylic acid tert-butyl ester.

Nitro group-containing ether compound represented by the formula (1) is a precursor of an aminoalcohol of the formula (18) disclosed in JP 2001-031631 A, and is a useful precursor of oseltamivir.

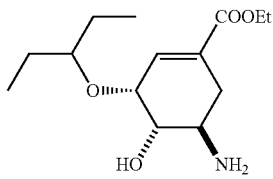

(18)

The dihydroxyhexenoic acid ester of the formula (4c) is subjected to oxidative diol-cleavage reaction by reacting with perhalogenic acid to prepare a formyl butenoic acid ester of the formula (2). The ester of the formula (2) is subjected to intramolecular cyclization by reacting with alkali metal hydrogen carbonate to prepare a nitrocyclohexene compound of the formula (1). The compound of the formula (1) is reduced by the reaction with zinc and HCl to obtain the aminoalcohol of the formula (18).

The dihydroxyhexenoic acid ester of the formula (4c) is subjected to oxidative diol-cleavage reaction by reacting with, for example, $HIO_4$ to prepare a formyl butenoic acid ester of the formula (2).

Specifically, the compound of the formula (4c) is dissolved in a solvent and then reacted with $HIO_4$. $HIO_4$ is usable in hydrate thereof such as $HIO_4 \cdot 2H_2O$ and can be used in an amount of 0.1 to 10 equivalents per equivalent of the compound (4c). Same solvents as above are used. The solvent can be used in an amount of 1 to 200 times of the reactants. The reaction is preferably conducted at −78 to 100° C., more preferably at 0 to 30° C. for 1 to 24 hours.

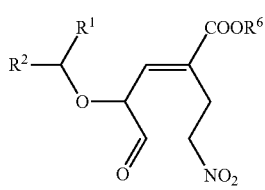

(2)

The formyl butenoic acid ester of the formula (2) is subjected to intramolecular nitroaldol reaction by reacting with $NaHCO_3$ to prepare the nitrocyclohexene compound of the formula (1). Specifically, the formyl butenoic acid ester is dissolved in a solvent and then reacted with $NaHCO_3$. $NaHCO_3$ can be used in an amount of 0.1 to 100 equivalents per equivalent of the formyl butenoic acid ester. The reaction is preferably conducted at −78 to 100° C., more preferably at 0 to 30° C. for 1 to 24 hours. Same solvents as above are used. The solvent can be used in an amount of 1 to 200 times of the reactants.

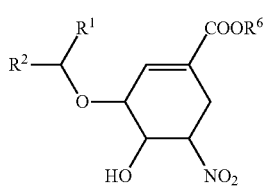

(1)

The nitrocyclohexene compound of the formula (1) is reduced by the reaction with, for example, zinc and HCl to obtain the aminoalcohol of the formula (18).

Specifically, the nitrocyclohexene is dissolved in a solvent and then reacted with zinc and HCl. Zinc is usable in powder thereof, etc and can be used in an amount of 0.1 to 100 equivalents per equivalent of the nitrocyclohexene. HCl is usable in 0.01 to 12N HCl aqueous solution and can be used in an amount of 0.1 to 100 equivalents per equivalent of the nitrocyclohexene. Same solvents as above are used. The solvent can be used in an amount of 1 to 200 times of the reactants. The reaction is preferably conducted at −78 to 100° C., more preferably at 0 to 30° C. for 1 to 24 hours. After completion of reaction, the reaction mixture is neutralized with aqueous solution of saturated $NaHCO_3$ or the like.

As mentioned above, the aminoalcohol of the formula (18) is disclosed in JP 2001-031631 A, and is a precursor of oseltamivir, and a useful precursor for preparing oseltamivir.

After completion of reaction, each of the above reaction products can be isolated and purified by the methods usually conducted in the isolation and purification of the organic compounds. For example, after completion of reaction, the reaction product can be extracted with a solvent such as hexane or like aliphatic hydrocarbon, toluene or like aromatic hydrocarbon, dichloromethane or like halogenated hydrocarbon, diethyl ether, diisopropyl ether or like ether. The extract is concentrated and the concentrate is purified by distillation, silica gel column chromatography, or the like.

EXAMPLES

The invention will be described in more detail with reference to the following reference examples and examples to which, however, the invention is not limited.

Example 1

Monocarboxylic Acid (5)

To a solution of a tartaric acid methyl ester-pentanone acetal (known compound, 1.0 g, 4.06 mmol) in MeOH (10 mL) was added 0.5 M KOH (7.3 mL, 0.9 eq.) at room temperature and the mixture was stirred for 10 minutes. To the mixture was added 1N hydrochloric acid for neutralization, then solvent is removed. The residue was purified by silica gel column to obtain monocarboxylic acid (5) (890.7 mg, 3.84 mmol, 94% yield) as a colorless oily substance.

Example 2

Hydroxyester (4a)

To a solution of monocarboxylic acid (5) (200 mg, 0.86 mmol) in THF (2.9 mL) was added $BH_3$—$SMe_2$ (10M, 0.26 mL, 3.0 eq.) at 0° C. and the mixture was stirred at room temperature for 2 hours. To the mixture was added water, extracted with ethyl acetate and dried with anhydrous sodium sulfate. The mixture was filtered and the filtrate was concentrated to remove a solvent. The crude product was purified by silica gel column to obtain hydroxyester (4a) (164 mg, 0.75 mmol, 87% yield) as a colorless oily substance.

$[\alpha]_D^{18}$+2.02 (c 1.09,$CHCl_3$)

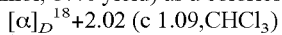H NMR (300 MHz,$CDCl_3$) δ 4.34(1H, d, J=8.2 Hz), 4.10 (1H, ddd, J=8.23, 4.12, 3.02 Hz), 3.87(1H, dd, J=12.08, 3.02 Hz), 3.70(3H, s), 3.66(1H, dd, J=12.07, 4.12 Hz), 2.56(1H, bs), 1.55-1.67(4H, m), 0.85(3H, t, J=7.41 Hz), 0.84(3H, t, J=7.14 Hz)

$^{13}$C NMR (75 MHz, $CDCl_3$) δ 170.9, 115.1, 79.3, 75.2, 61.8, 52.1, 29.5, 29.4, 7.9, 7.3

IR (neat) 3418, 2972, 1714, 1215$cm^{-1}$ $R_f$=3.66 (hexane/AcOEt=2/1)

Example 3

THP Ester (4b)

To a solution of hydroxyester (4a) (2.31 g, 10.6 mmol) in dichloromethane (35 mL) were added 3,4-dihydro-2H-pyran (1.9 mL, 21.2 mmol, 2.0 eq.) and (+)camphor sulfonic acid (123 mg, 0.5 mmol, 0.05 eq.) at 0° C. and the mixture was stirred at room temperature for 30 minutes. To the mixture was added $NaHCO_3$ solution for neutralization, then dried with anhydrous sodium sulfate. The mixture was filtered and the filtrate was concentrated to remove a solvent. The crude product was purified by silica gel column to obtain a mixture of diastereomers of THP ester (4b) (3.2 g, 10.58 mmol, more than 99 yield) as a colorless oily substance.

$^1H$ NMR (300 MHz, $CDCl_3$) δ 4.34(1H, d, J=8.2 Hz), 4.10 (1H, ddd, J=8.23, 4.12, 3.02 Hz), 3.87(1H, dd, J=12.08, 3.02 Hz), 3.70(3H, s), 3.66(1H, dd, J=12.07, 4.12 Hz), 2.56(1H, bs), 1.55-1.65(4H, m), 0.85(3H, t, J=7.41 Hz), 0.84(3H, t, J=7.14 Hz)

$R_f$=0.50 (hexane/AcOEt=1/1)

Example 4

Acetoxy Unsaturated Ester (3b)

To a solution of THP ester (4b) (730 mg, 2.30 mmol) in toluene (11.5 mL) was added DIBAL-H (2.55 mL, 2.53 mmol, 1.1 eq.) at −48° C. and the mixture was stirred for 1 hour. To the mixture were added ethanol and water, then filtered with use of celite. The filtrate was concentrated to remove a solvent to obtain a colorless oily substance (690 mg) which was used for next reaction without purification. To the crude product (690 mg) were added ethyl acrylate (1.15 mL, 10.6 mmol, 4.6 eq.) and 1,4-diazabicyclo[2.2.2]octane (258 mg, 2.30 mmol, 1.0 eq.) at room temperature and the mixture was stirred for 5 days. The mixture was concentrated to remove a solvent to obtain a colorless oily substance (725 mg) which was used for next reaction without purification. To a solution of crude product (725 mg) in THF (4.6 mL) were added triethylamine (0.96 mL, 6.9 mmol, 3.0 eq.), acetic anhydride (0.43 mL, 4.6 mmol, 2.0 eq.) and N-dimethylaminopyridine (84.3 mg, 0.69 mmol, 0.3 eq.) at 0° C. and the mixture was stirred for 30 minutes. To the mixture was added water, extracted with ethyl acetate, washed with water and dried with anhydrous sodium sulfate. The mixture was filtered and the filtrate was concentrated to remove a solvent. The crude product was purified by silica gel column to obtain a mixture of diastereomers of acetoxy unsaturated ester (3b) (504 mg, 1.21 mmol, 53 95 yield, three steps) as a colorless oily substance.

$^1H$ NMR (300 MHz, $CDCl_3$) δ 6.41-6.39(1H, m), 5.77-5.76(2H, m), 4.65-4.61(1H, m), 4.33-3.98(8H, m), 3.93-3.37 (6H, m), 2.12-2.10(3H, m), 1.70-1.60(4H, m), 0.96-0.86(6H, m)

$R_f$=0.60 (hexane/AcOEt=1/1)

Example 5

Nitroester (2b)

To a solution of nitromethane (0.46 mL, 8.43 mmol, 15 eq.) in ethanol (1.0 mL) was added KOH (0.61 mmol, 1.1 eq.) at 0° C. and the mixture was stirred for 30 minutes. To the mixture was added a solution of the compound (3b) (233 mg, 0.56 mmol) in ethanol (0.9 mL) at 0° C. and the mixture was stirred at room temperature for 4 hours. The mixture was concentrated to remove a solvent, neutralized with a saturated aqueous solution of ammonium chloride and extracted with ethyl acetate. The extract was dried with anhydrous sodium sulfate and concentrated to remove a solvent. The crude product was purified by silica gel column to obtain a mixture of diastereomers of nitroester (2b) (154 mg, 0.37 mmol, 66% yield) as a colorless oily substance $^1H$ NMR (300 MHz, $CDCl_3$) δ 6.41-6.39(1H, m), 5.77-5.76(2H, m), 4.65-4.61(1H, m), 4.33-3.98(8H, m), 3.93-3.37 (6H, m), 2.12-2.10(3H, m), 1.70-1.60(4H, m), 0.96-0.86(6H, m)

$R_f$=0.60 (hexane/AcOEt=1/1)

Example 6

Hydroxynitroester (2a)

To a solution of nitroester (2b) (27 mg, 0.065 mmol) in ethanol (0.6 mL) were added water (0.3 mL) and 1N HCl (0.2 mL, 0.6 eq.) at 0° C. and the mixture was stirred at room temperature for 1 hour. The mixture was neutralized with a saturated aqueous solution of $NaHCO_3$ and dried with anhydrous sodium sulfate. The mixture was filtered and the filtrate was concentrated to remove a solvent. The crude product was purified by silica gel column to obtain hydroxynitroester (2a) (19.7 mg, 0.059 mmol, 92% yield) as a colorless oily substance.

$[\alpha]_D^{18}$ +18.26 (c 0.36, $CHCl_3$)

$^1H$ NMR (300 MHz, $CDCl_3$) δ 6.83(1H, d, J=8.5 Hz), 4.74(1H, t, J=8.5 Hz), 4.57(2H, dt, J=7.4, 1.4 Hz), 4.25(4H, q, J=7.1 Hz), 3.85-3.93(2H, m), 3.62(1H, m), 3.12(2H, t, J=6.9 Hz), 1.71(4H, m), 1.33(3H, t, J=7.1 Hz), 0.96(3H, t, J=7.4 Hz), 0.94(3H, t, J=7.7 Hz)

$^{13}C$ NMR (75 MHz, $CDCl_3$) δ 166.2, 140.9, 131.7, 114.5, 81.8, 74.6, 74.0, 62.1, 61.4, 31.2, 31.1, 26.5, 15.0, 8.9, 8.8

IR (neat): 3460, 1709, 1554 $cm^{-1}$ $R_f$=0.17 (hexane/AcOEt=3/1)

Example 7

Dihydroxyhexenoic Acid Ester (4c)

To a solution of hydroxynitroester (2a) (300 mg, 0.905 mmol) in methylene chloride (3 mL) was added $BH_3$—$SMe_2$ (1M, 0.99 mL, 0.995 mmol, 1.1 eq.) at 0° C. and the mixture was stirred at room temperature for 1 hour. To the mixture was added $BF_3OEt_2$ (0.12 mL, 0.995 mmol, 1.1 eq.) at 0° C. and the mixture was stirred for 30 minutes, and further at room temperature for 30 minutes. To the mixture was added methanol and the mixture was concentrated to remove a solvent. The crude product was purified by silica gel column to obtain dihydroxyhexenoic acid ester (4c) (281 mg, 0.842 mmol, 93% yield) as a colorless oily substance.

$[\alpha]_D^{18}$ −18.76 (c 2.14, $CHCl_3$)

$^1H$ NMR (300 MHz, $CDCl_3$) δ 6.80(1H, d, J=9.3 Hz), 4.53-4.68(2H, m), 4.40(1H, dd, J=6.6, 9.3 Hz), 4.25(2H, m), 3.78(1H, dd, J=8.2, 3.6 Hz), 3.60(1H, dt, J=6.9, 6.6 Hz), 3.49(1H, dd, J=8.2, 3.6 Hz), 3.09-3.25(2H, m), 2.90-2.99(1H, m), 1.39-1.64(4H, m), 1.33(3H, t, J=7.1 Hz), 0.92(3H, t, J=7.4 Hz), 0.88(3H, t, J=7.4 Hz)

$^{13}C$ NMR (75 MHz, $CDCl_3$) δ 165.7, 143.3, 130.1, 80.6, 74.4, 73.8, 73.6, 62.7, 61.4, 26.7, 25.8, 25.7, 14.2, 9.9, 9.2

IR (neat) 3425, 2969, 1705, 1554, 1215 $cm^{-1}$ $R_f$=0.20 (hexane/AcOEt=1/1)

Example 8

Mannitol Triacetal (11)

To a solution of 3-pentanone (14.5 mL, 137 mmol, 5 eq.) in THF (15 mL) were added ethyl orthoformate (10.5 mL, 95.9 mmol, 10.5 eq.) and DL-10-camphor sulfonic acid (640 mg, 2.74 mmol, 0.1 eq.) at room temperature. After the solution was stirred at 60° C. for 2.5 hours and further at room temperature for 17 hours, D-(−)-mannitol (5.0 g, 27.4 mmol) was added thereto. After the reaction mixture was stirred at 60° C. for 3 hours and further 70° C. for 21 hours, triethylamine (0.4 mL, 2.74 mmol, 0.1 eq.) was added thereto at room temperature. The mixture was concentrated to remove a solvent and was purified by silica gel column to obtain mannitol triacetal (11) (10.3 g, 97% yield) as a colorless oily substance.

$[\alpha]_D^{18}$ +21.8 (c 1.55, $CHCl_3$)

$^1$H NMR (300 MHz, $CDCl_3$) δ 0.82-0.95(m, 18H), 1.55-1.72(m, 12H), 3.90(dd, 2H, 3=1.6, 4.1 Hz), 4.07(dd, 2H, 3=6.3, 8.0 Hz), 4.14-4.20(m, 2H)

$^{13}$C NMR (75 MHz, $CDCl_3$) δ 7.8, 7.9, 8.0, 29.1, 29.5, 30.1, 66.9, 76.7, 79.9, 113.26, 113.34

IR (neat) 2980, 1556, 1222 $cm^{-1}$ $R_f$ 0.4 (hexane:EtOAc=20:1)

Example 9

Aldehyde (10)

To a solution of mannitol triacetal (11) (404 mg, 1.05 mmol) in THF (4 mL) were added ethylene glycol (0.06 mL, 1.15 mmol, 1.1 eq.) and methane sulfonic acid (0.003 mL, 0.0524 mmol, 0.05 eq.) and the mixture was stirred at room temperature for 3 hours. To the mixture was added $HIO_4 \cdot 2H_2O$ (287 mg, 1.30 mmol, 1.2 eq.) and the mixture was stirred at room temperature for 0.5 hour. The mixture was neutralized with a saturated aqueous solution of $NaHCO_3$ (1 mL) and dried with anhydrous sodium sulfate. The mixture was filtered and the filtrate was concentrated to remove a solvent. The crude product was purified by silica gel column to obtain aldehyde (10) (210 mg, 70% yield) as a colorless oily substance.

$[\alpha]_D^{18}$ +12.8 (c 1.55, $CHCl_3$)

$^1$H NMR (300 MHz, $CDCl_3$) δ 0.90-0.97(m, 12H), 1.58-1.74(m, 8H), 3.82-4.20(m, 4H), 4.40(dd, 1H, J=1.4, 7.0 Hz)

$^{13}$C NMR (75 MHz, $CDCl_3$) δ 7.2, 7.5, 7.7(2C), 28.3, 29.2, 29.3, 29.6, 67.3, 76.1, 76.6, 113.5, 115.4, 198.5

IR (neat) 2972, 1711, 1215 $cm^{-1}$ $R_f$ 0.3 (hexane : EtOAc=2:1)

Example 10

Acetoxy Unsaturated Ester (9)

To aldehyde (10) (255 mg, 0.892 mmol) were added ethyl acrylate (0.2 mL, 1.78 mmol, 2 eq.) and 1,4-diazabicyclo[2.2.2]-octane (100 mg, 0.892 mmol, 1 eq.) at room temperature and the mixture was stirred at 30° C. for 3 days. After cooled to room temperature, to the mixture were added triethylamine (0.25 mL, 1.78 mmol, 2 eq.) and acetic anhydride (0.17 mL, 1.78 mmol, 2 eq.) and stirred for 0.5 hour. To the mixture was added EtOH (1 mL) and the mixture was concentrated to remove a solvent. The crude product was purified by silica gel column to obtain acetoxy unsaturated ester (9) (269 mg, 70% yield) as a colorless oily substance.

$^1$H NMR (300 MHz, $CDCl_3$) δ 0.75-0.98(m, 12H), 1.29(t, 3H, J=7.2 Hz), 1.50-1.75(m, 8H), 2.03 and 2.07 (2s, 3H), 3.72-4.30(m, 6H), 4.60-4.78(m, 1H), 5.80-6.40(m, 3H)

$R_f$ 0.4 (hexane:EtOAc=5:1)

Example 11

Nitroester (8)

To a solution of acetoxy unsaturated ester (9) (226.5 mg, 0.529 mmol) in EtOH (2 mL) were added KOH (36 mg, 0.634 mmol, 1.2 eq.) and a solution of nitromethane (0.85 mL, 15.9 mmol, 30 eq.) in EtOH (3 mL) at room temperature and the mixture was stirred for 4.5 hours. To the mixture were added 6N HCl for neutralization and diluted with ethyl acetate, then dried with anhydrous sodium sulfate. The mixture was filtered and the filtrate was concentrated to remove a solvent. The crude product was purified by silica gel column to obtain nitroester (8) (169 mg, 75% yield) as a colorless oily substance.

$[\alpha]_D^{18}$ +7.95 (c 1.55, $CHCl_3$)

$^1$H NMR (300 MHz, $CDCl_3$) δ 0.76-0.98(m, 12H), 1.32(t, 3H, J=7.1 Hz), 1.54-1.74(m, 8H), 3.06-3.25(m, 2H), 3.68(t, 1H, J=7.6 Hz), 3.92(dd, 1H, J=3.1, 10.1 Hz) 4.02-4.15(m, 1H), 4.16-4.28(m, 3H), 4.55-4.62(m, 2H), 4.68(t, 1H, J=8.2 Hz), 6.86(d, 1H, J=8.2 Hz)

$^{13}$C NMR (75 MHz, $CDCl_3$) δ 8.0, 8.2(2C), 8.3, 14.3, 25.8, 28.7, 29.7, 30.43, 30.46, 61.2, 68.5, 73.6, 77.0, 81.8, 113.7, 114.3, 129.8, 140.8, 165.9

IR (neat) 2981, 1712, 1620, 1217 $cm^{-1}$ $R_f$ 0.4 (hexane:EtOAc=4:1)

Example 12

Nitrodiol (7)

To a solution of nitroester (8) (99 mg, 0.230 mmol) in EtOH (4 mL) was added DL-10-camphor sulfonic acid (53 mg, 0.023 mmol, 0.1 eq.) and the mixture was stirred at room temperature for 24 hours. To the mixture was added triethylamine (0.064 mL, 0.046 mmol, 0.2 eq.) for neutralization. The mixture was concentrated to remove a solvent. The crude product was purified by silica gel column to obtain nitrodiol (7) (81 mg, 98% yield) as a colorless oily substance.

$[\alpha]_D^{18}$ +15.9 (c 1.55, EtOH)

$^1$H NMR (300 MHz, $CDCl_3$) δ 0.91(t, 3H, J=7.2 Hz), 0.98(t, 3H, J=7.2 Hz), 1.32(t, 3H, J=7.2 Hz), 1.67(q, 4H, J=7.2 Hz), 2.46-2.58(bs, 2H), 3.14(t, 2H, J=7.1 Hz), 3.62-3.70(m, 1H), 3.72-3.88(m, 3H), 4.24(dq, 2H, J=1.3, 7.1 Hz), 4.50-4.63(m, 2H), 4.72(dd, 1H, J=6.6, 8.5 Hz), 6.84(d, 1H, J=8.5 Hz)

$^{13}$C NMR (75.5 Hz, $CDCl_2$) δ 8.2, 14.3, 26.0, 30.47, 30.51, 61.4, 64.1, 72.9, 74.0, 75.7, 81.1, 114.2, 130.4, 141.0, 165.9

IR (neat) 3427, 2972, 1710, 1220 $cm^{-1}$ $R_f$ 0.3 (hexane:EtOAc=2:1)

Example 13

Formyl Nitroester (6)

To a solution of nitrodiol (7) (81 mg, 0.22 mmol) in THF (2 mL) were added $HIO_4 \cdot 2H_2O$ (62 mg, 0.27 mmol, 1.2 eq.) and the mixture was stirred at room temperature for 0.5 hour. The mixture was dried with anhydrous sodium sulfate. The mixture was filtered and the filtrate was concentrated to remove a solvent. The crude product was purified by silica gel column to obtain formyl nitroester (6) (62 mg, 85% yield) as a colorless oily substance.

$^1$H NMR (300 MHz, CDCl$_3$) δ 0.92(t, 3H, J=7.2 Hz), 0.97(t, 3H, J=7.2 Hz), 1.33(t, 3H, J=7.2 Hz), 1.68(q, 4H, J=7.2 Hz), 3.14(t, 2H, J=7.1 Hz), 4.25(q, 2H, J=7.1 Hz), 4.52-4.64(m, 4H), 6.84(d, 1H, J=8.5 Hz), 9.76(d, 1H, J=1.4 Hz)

Example 14

Hydroxy Nitroester (2a)

To a solution of formyl nitroester (6) (62 mg, 0.19 mmol) in THF (2 mL) was added NaBH$_4$ (7 mg, 0.19 mmol, 1.0 eq.) and the mixture was stirred at room temperature for 1 hour. To the mixture were added 0.1N HCl (0.5 mL) for neutralization and dried with anhydrous sodium sulfate. The mixture was filtered and the filtrate was concentrated to remove a solvent. The crude product was purified by silica gel column to obtain hydroxy nitroester (2a) (60 mg, 95% yield) as a colorless oily substance. NMR data was the same as those of the compound (2a) of Example 6.

Example 15

D-Arabinose-4,5-O-Acetal Compound (14)

To a solution of diethyl ketone dimethyl acetal (3.97 g, 1.5 eq.) in dimethyl formamide (30 mL) were added D-arabinose (3.0 g, 20.0 mmol) and p-toluene sulfonic acid (0.19 g, 0.05 eq.) at 0° C. and the mixture was stirred at room temperature for 20 hours. To the mixture were added triethylamine (0.28 mL, 0.1 eq.) for neutralization and the mixture was concentrated to remove a solvent. The crude product was purified by silica gel column using ethyl acetate-hexane mixed solvent to obtain D-arabinose-4,5-O-acetal compound (14) {1.93 g, 79% yield (56% conversion)} as a colorless oily substance.

$^1$H NMR (300 MHz, CDCl$_3$) δ 0.90(t, 3H, J=7.1 Hz), 0.96(t, 3H, J=7.1 Hz), 1.64(q, 2H, J=7.1 Hz), 1.74(q, 2H, J=7.1 Hz), 2.40-2.50(b, 1H), 2.93-3.02(b, 1H), 3.84(dd, 1H, J=2.1, 12.8 Hz), 3.93(dt, 1H, J=3.6, 5.2 Hz), 4.14(dd, 1H, J=2.9, 12.8 Hz), 4.23-4.29(m, 1H), 4.34(dd, 1H, J=5.1, 6.7 Hz), 5.20(dd, 1H, J=3.6,4.1 Hz);

$^{13}$C NMR (75 MHz, CDCl$_3$) δ 8.9, 9.2, 29.1, 30.3, 61.1, 70.2, 72.7, 75.7, 92.0, 113.9; IR(neat) 2980, 1556, 1222cm$^{-1}$;
R$_f$ 0.5 (AcOEt)

Example 16

Formyl Dioxolane compound (13)

To a solution of D-arabinose-4,5-O-acetal compound (14) (3.25 g, 14.9 mmol) in THF/H$_2$O (15 mL/6 mL) were added KIO$_4$ (5.14 g, 1.5 eq.) at room temperature and the mixture was stirred for 22 hours. After the reaction, the mixture was diluted with ethyl acetate and dried with anhydrous sodium sulfate. The mixture was filtered with celite and the filtrate was concentrated to remove a solvent. The crude product was purified by silica gel column using ethyl acetate-hexane mixed solvent to obtain formyl dioxolane compound (13) (2.90 g, 90% yield) as a colorless oily substance.

$^1$H NMR (300 MHz, CDCl$_3$), δ 0.91(t, 3H, J=7.2 Hz), 0.98(t, 3H, J=87.1 Hz), 1.65(q, 2H, J=7.1 Hz), 1.80(q, 2H, J=7.1 Hz), 4.08(ddd, 1H, J=0.8, 4.9, 12.1 Hz), 4.47(dd, 1H, J=2.2, 8.2 Hz), 4.53(ddd, 1H, J=0.8, 3.3, 12.1 Hz), 4.58-4.64 (m, 1H), 8.02(s, 1H), 9.73(d, 1H, J=2.4 Hz);

$^{13}$C NMR (75 MHz, CDCl$_3$) δ 7.9, 8.7, 28.9, 29.2, 61.1, 76.2, 80.4,
R$_f$ 0.50 (hexane/AcOEt=2/1)

Example 17

Acetoxy Unsaturated Ester (12)

To formyl dioxolane compound (13) (0.417 g, 1.93 mmol) were added ethyl acrylate (0.63 mL, 3.0 eq.) and DABCO (0.32 g, 1.5 eq.) at room temperature and the mixture was stirred for 90 hours. After the reaction, ethyl acrylate and DABCO were removed under reduced pressure. The crude product was dissolved in THF (3 mL) and thereto were added triethylamine (1.34 mL, 5 eq.) and acetic anhydride (0.55 mL, 3 eq.) at 0° C. and the mixture was stirred for 30 minutes. After adding ethanol (2 mL), the mixture was concentrated to remove a solvent. The crude product was purified by silica gel column using ethyl acetate-hexane mixed solvent to obtain acetoxy unsaturated ester (12) (284 mg, 41 % yield) as a colorless oily substance.

$^1$H NMR (300 MHz, CDCl$_3$) δ 0.88(t, 6H, J=7.1 Hz), 1.31(t, 3H, J=7.1 Hz), 1.64(q, 4H, J=7.1 Hz), 2.12(s, 3H), 4.07(m, 1H), 4.18(m, 2H), 4.24(q, 2H, J=7.1 Hz), 4.40(dt, 1H, J=1.2, 9.9 Hz), 5.88(d, 1H, J=4.7 Hz), 5.90(s, 1H), 6.42(s, 1H), 8.07(s, 1H);

$^{13}$C NMR (75 MHz, CDCl$_3$) δ 8.0, 8.2, 14.3, 21.2, 30.3, 30.6, 61.5, 64.2, 70.8, 75.7, 114.2, 128.0, 136.9, 160.8, 165.0, 169.5;
IR (neat) 2980, 1556, 1222cm$^{-1}$;
R$_f$ 0.53 (hexane/AcOEt=2/1)

Example 18

Hydroxynitroester (2a)

To a solution of acetoxy unsaturated ester (12) (0.138 g, 0.38 mmol) in ethanol (3 mL) were added nitromethane (0.41 mL, 20 eq.) and an aqueous solution of (1 mL) of KOH (0.064 g, 3.0 eq.) and the mixture was stirred at room temperature for 2 hours. After the reaction, the mixture was diluted with ethyl acetate and dried with anhydrous sodium sulfate. The mixture was filtered with celite and the filtrate was concentrated to remove a solvent. The crude product was purified by silica gel column using ethyl acetate-hexane mixed solvent to obtain hydroxynitroester (2a) (0.862 g, 68% yield) as a colorless oily substance. NMR data was the same as those of the compound (2a) of Example 6.

Example 19

Formyl Butenoic Acid Ester (2)

To a solution of dihydroxyhexenoic acid ester (4c) (38 mg, 0.11 mmol) in THF (1.4 mL) was added HIO$_4$·2H$_2$O (31 mg, 0.13 mmol, 1.2 eq.) at 0° C. and the mixture was stirred for 1 hour. The mixture was extracted with ethyl acetate and dried with anhydrous sodium sulfate. The mixture was filtered and the filtrate was concentrated to remove a solvent to obtain formyl butenoic acid ester (2) (33 mg, 0.11 mmol, 100% yield) as a colorless oily substance.

$^1$H NMR (300 Hz, CDCl$_3$) δ 9.70(1H, d, J=3.8 Hz), 6.88-6.90(1H, m), 5.11-5.05(1H, m), 4.50-4.55(2H, m), 4.25(2H, q, J=7.1 Hz), 3.44(1H, quin, J=5.5 Hz), 3.14-3.00(2H, m), 1.45-1.64(4H, m), 1.32(3H, t, J=7.1 Hz), 0.86-0.96(6H, m)

Example 20

Nitrocyclohexene (1)

To a solution of formyl butenoic acid ester (2) (33 mg, 0.11 mmol) in THF (1.4 mL) was added an aqueous solution (1.5 mL) of $NaHCO_3$ (96 mg, 1.13 mmol, 10 eq.) and the mixture was stirred at 0° C. for 10 minutes and further at room temperature for 4 hours. The mixture was extracted with ethyl acetate and dried with anhydrous sodium sulfate. The mixture was filtered and the filtrate was concentrated to remove a solvent. The crude product was purified by silica gel column to obtain nitrocyclohexene (1) (18.4 mg, 0.061 mmol, 56% yield) as a colorless oily substance.

$[\alpha]_D^{18}$ −65.58 (c 0.61, $CHCl_3$)

$^1H$ NMR (300 MHz, $CDCl_3$) δ 6.86-6.88(1H, m), 4.78(1H, ddd, J=1.9, 5.8, 10.2 Hz), 4.54(1H, m), 4.25(1H, q, J=7.1 Hz), 4.24(1H, q, J=7.1 Hz), 4.06-4.09(1H, m), 3.41(1H, quin, J=5.5 Hz), 3.07-3.14(1H, m), 2.90-3.00(1H, m), 1.45-1.64 (4H, m), 1.32(3H, t, J=7.1 Hz), 0.86-0.96(6H, m)

$^{13}C$ NMR(75 MHz, $CDCl_3$) δ 165.1, 133.6, 129.5, 82.6, 73.8, 68.6, 61.2, 26.8, 26.6, 24.9, 10.1, 9.6

IR (neat):3463, 2942, 2884, 1756, 1215$cm^{-1}$ $R_f$=0.4 (hexane/AcOEt=2/1)

Example 21

Aminoalcohol (18)

To a solution of nitrocyclohexene (1) (75 mg, 0.248 mmol) in ethanol (2 mL) were added zinc powder (98 mg, 1.49 mmol, 6.0 eq.) and 1N HCl (1 mL, 0.4 eq.) at room temperature and the mixture was stirred for 12 hours. To the mixture was added a saturated solution of $NaHCO_3$ for neutralization and dried with anhydrous sodium sulfate. The mixture was filtered with celite and the filtrate was concentrated to remove a solvent. The crude product was purified by silica gel column to obtain aminoalcohol (18) (81 mg, 100% yield).

$^1H$ NMR (300 MHz, $CD_3OD$) δ 6.77-6.80(1H, m), 4.20 (2H, q, J=7.1 Hz), 3.96(1H, t, J=3.8 Hz), 3.82(1H, t, J=2.5 Hz), 3.42(1H, quin, J=5.8, Hz), 3.13(1H, ddd, J=11.5, 5.5, 2.2 Hz), 2.58(1H, dd, J=17.5, 5.2 Hz), 2.20-2.30(1H, m), 1.62-1.45(4H, m), 1.29(3H, t, J=7.1 Hz), 4.11(6H, q, J=7.4 Hz)

INDUSTRIAL APPLICABILITY

Nitro group-containing ether compound of the present invention can be prepared by using as a starting material D-tartaric acid, mannitol or arabinose which is present in extremely abundant quantities as natural source or industrial material, via 1,3-dioxolane compound. It is possible to produce oseltamivir safely and stably in large quantities with use of the nitro group-containing ether compound.

The invention claimed is:

1. A nitro group-containing ether compound of the formula (1)

(1)

wherein $R^1$, $R^2$ and $R^6$ are the same or different and are each alkyl, aryl, substituted aryl, aralkyl, substituted aralkyl or aromatic heterocyclic group, and $R^1$ and $R^2$ are not methyl simultaneously.

2. The compound as defined in claim 1 wherein $R^1$, $R^2$ and $R^6$ are the same or different and are each a straight-chain, branched chain or cyclic alkyl having 1 to 8 carbon atoms, aralkyl having 7 to 20 carbon atoms or aralkyl having 7 to 20 carbon atoms and having a substituent, the substituent of aralkyl having 7 to 20 carbon atoms being selected from the group consisting of alkyl having 1 to 8 carbon atoms, alkoxy having 1 to 8 carbon atoms, halogen atom, hydroxyl, amino and trifluoromethyl.

3. A process for preparing a compound of the formula (1) comprising subjecting a compound of the formula (2) to intramolecular nitroaldol reaction, (2)

(1)

wherein $R^1$, $R^2$ and $R^6$ are the same or different and are each alkyl, aryl, substituted aryl, aralkyl, substituted aralkyl or aromatic heterocyclic group, and $R^1$ and $R^2$ are not methyl simultaneously.

4. A process for preparing a compound of the formula (3) comprising reducing a compound of the formula (1), (1)

(3)

wherein $R^1$, $R^2$ and $R^6$ are the same or different and are each alkyl, aryl, substituted aryl, aralkyl, substituted aralkyl or aromatic heterocyclic group, and $R^1$ and $R^2$ are not methyl simultaneously.

* * * * *